United States Patent [19]
Bromet

[11] Patent Number: 5,879,710
[45] Date of Patent: Mar. 9, 1999

[54] HETEROFUNCTIONAL MUCOADHESIVE PHARMACEUTICAL DOSAGE COMPOSITION

[75] Inventor: Norbert E. Bromet, Orléans-la-Source, France

[73] Assignee: Biotec Centre S.A., Orleans Cedex 2, France

[21] Appl. No.: 716,463

[22] PCT Filed: Mar. 31, 1995

[86] PCT No.: PCT/FR95/00417

§ 371 Date: Dec. 10, 1996

§ 102(e) Date: Dec. 10, 1996

[87] PCT Pub. No.: WO95/26713

PCT Pub. Date: Oct. 12, 1995

[30] Foreign Application Priority Data

Apr. 1, 1994 [FR] France ................................ 94 03895

[51] Int. Cl.⁶ .................................................. A61K 9/00
[52] U.S. Cl. .......................................... 424/487; 424/484
[58] Field of Search ................................... 424/422, 426, 424/428, 434, 435, 436, 484, 486, 487, 494, 495

[56] References Cited

U.S. PATENT DOCUMENTS

| | | |
|---|---|---|
| 4,250,163 | 2/1981 | Nagai . |
| 4,470,846 | 9/1984 | Sandyk ..................................... 514/159 |
| 4,740,365 | 4/1988 | Yukimatsu et al. ..................... 424/435 |

FOREIGN PATENT DOCUMENTS

| | | |
|---|---|---|
| 0 020 777 | 1/1981 | European Pat. Off. . |
| 0 159 604 | 10/1985 | European Pat. Off. . |
| 0 196 700 | 10/1986 | European Pat. Off. . |
| 0 255 827 | 3/1992 | European Pat. Off. . |
| 0 518 468 | 12/1992 | European Pat. Off. . |
| 87 04342 | 7/1987 | WIPO . |
| 91 06290 | 5/1991 | WIPO . |

*Primary Examiner*—Marian C. Knode
*Assistant Examiner*—Brenda G. Brumback
*Attorney, Agent, or Firm*—Nixon & Vanderhye PC

[57] ABSTRACT

A mucoadhesive controlled-release pharmaceutical formulation comprising at least one active principle selected from the group consisting of melatonin and melatonin derivatives, composed of a first layer and a second layer, the first layer being mucoadhesive and permitting a sustained release of the active principle, and the second layer being nonmucoadhesive, and permitting a rapid release of the active principle.

14 Claims, 1 Drawing Sheet

HETEROFUNCTIONAL MUCOADHESIVE PHARMACEUTICAL DOSAGE COMPOSITION

The present invention relates to a pharmaceutical dosage formulation enabling products such as melatonin or its derivatives to be administered, by combining a loading dose permitting a rapid action and, in the case of melatonin (or its derivatives), a clear chronobiological signal and one or more doses released gradually, enabling products to be made available rapidly, and in a sustained manner, in the body.

Generally speaking, the present invention relates to any mucoadhesive formulation combining at least two formulations affording controlled released of different rates, ranging from a rapid form to a sustained-release form.

The product is especially advantageous when the formulation is applied to a joint administration via the transmucosal or sublingual route and via the oral route, where the pharmaceutical dosage formulation combines a rapid oral form with a controlled-release oral form and a transmucosal form within a single mucoadhesive buccal tablet.

Melatonin (N-acetyl-5-methoxytryptamine) is an endogenous hormone synthesized by the epiphysis (or pineal gland) and involved, inter alia, in the regulation of the circadian rhythm, in the inhibition of gonadal development and in the regulation of ovulation.

It has the special feature of being released during the night only in mammals, and especially in human being.

In the body, this molecule is catabolized in the liver and kidneys to form, inter alia, 6-hydroxymelatonin.

An important feature of melatonin is its very marked circadian rhythm of secretion; in effect, the plasma levels of this hormone are low during the day (less than 10 pg/ml) and are high during the night (of the order of 70 pg/ml) in human being (1, 2).

The relationship between the melatonin cycle, that is to say its variations in concentration in the plasma, and the sleep cycle is not clear, but melatonin may assist in organizing or reorganizing the circadian cycles.

In the present application, melatonin and its derivatives will be used and described as active principles administered in the heterofunctional mucoadhesive pharmaceutical dosage composition.

It represents an especially significant example precisely as a result of the features of the action of this compound, which must both reach the systemic circulation rapidly and concomitantly afford a gradual release, thus enabling the product to be made available immediately and then in a sustained manner.

Any type of compound, such as melatonin derivatives substituted at position 2 or position 6 with halogens, or alternatively any other derivative as described in Patent Applications WO88/07367 or WO89/04659, or other substances having a pharmacological effect necessitating both a rapid release ranging from a flash type release to a slow and controlled type release, may be advantageously introduced into the pharmaceutical dosage formulation of the invention.

Melatonin and its derivatives, bearing in mind their feature of being a regulatory factor of the circadian system, are usable, for example, during a journey across time zones for treating the phenomenon of jet lag (3). During this period, most people suffer from, among other symptoms, mood disorders, sleep disturbance and a modification of alertness during the daytime; various studies show, in actual fact, an improvement in the symptoms of jet lag after a melatonin-based treatment; more recently, it was shown that subjects who underwent 6- to 12-hour time shifts showed a faster resynchronization of the different circadian rhythms (6-sulfatoxymelatonin, cortisol, temperature, urinary electrolytes, and the like) after a treatment with melatonin (4, 5).

Other applications of the regulation of circadian rhythms conferred by administration of melatonin are, in particular:

shift work:

it has been shown that the intake of melatonin at bedtime by individuals subjected to different types of shift work (7-day shift, gradual changes, and the like) improves the quality and duration of sleep and alertness during the period of activity (6);

blind subjects:

these subjects no longer perceive light, the main synchronizing factor of their circadian clock. Most of them nevertheless keep this clock correctly actuated in time with the day/night rhythm, probably because other signals, such as social activities, take over from the light environment. However, the circadian clock of some blind people is no longer synchronized and adopts an unfettered course, that is to say with its own period which can vary from 22 to 30 hours (7).

This leads to an alternation of periods which are favorable and unfavorable for these subjects in accordance with the synchronization or lack of synchronization relative to the day/night cycles; melatonin should hence enable the circadian clock of these blind people to be synchronized, and make this alternation between favorable and unfavorable periods disappear;

phase-delay insomnia:

some subjects suffer from "delayed sleep" syndrome. This syndrome manifests itself in difficulties in falling asleep, difficulty in waking up, poor alertness and a reduced level of performance. This syndrome results from a time shift in the circadian clock relative to its external synchronizing factors. Taking melatonin approximately 2 hours before bedtime reduces by 2 hours the interval between retiring and sleep, and also improves the quality of the sleep (8);

this applies also, and more generally, to subjects who have disturbed or poor quality sleep associated or otherwise with a pathology, a chronic fatigue syndrome, anxiety or depression, or with the subject's age, given that nocturnal melatonin concentrations decrease with subjects' age (9).

cancer:

melatonin administered chronically during the afternoon (50 to 500 µg) can inhibit the growth of dimethylbenzanthracene (DMBA)-induced malignant mammary tumors in rats (10).

Moreover, positive effects of melatonin on the progression of certain types of cancer (prostate, pituitary, melanoma, leukemia, and the like) have been observed experimentally in rats or mice (11); in man, some reports have suggested the therapeutic efficacy of melatonin in the treatment of carcinoma of the lung, stomach or breast, or of leukemia (11, U.S. Pat. No. 4,855,305).

It has also been shown that there is an effect of melatonin on seasonal stress (12).

The applications of melatonin and its derivatives are very numerous, are described in various publications (Patents EP513702, EP438856, WO90/14084, WO88/07367, WO89/04659) and are incorporated in this patent application by way of reference.

All melatonin derivatives, analogs and homologs as described, for example, in U.S. Pat. No. 4,880,826, WO87/0432 and WO89/04659 in particular, are also incorporated by reference in the present application, as advantageous active principles of the invention.

It appears, however, that no administration route which has been described has the requisite qualities of administration of these compounds in order, in particular, to reestablish the internal clock and the circadian cycles, which qualities are on the one hand qualities of well-being since this treatment is often directed towards persons in good health, and on the other hand qualities of short-term rapid efficacy lasting sufficiently long for there actually to be a reestablishment of the rhythm with reestablishment of the different chronobiological markers as are mentioned above.

Various dosage forms have been proposed. There may be mentioned as an example Patent Application WO93/07870, which is a device for transdermal administration of melatonin. This patent application claims the use of the already known and marketed transdermal system, for particular application to melatonin.

Patent Application WO91/0690 is a homogeneous bioadhesive composition which permits adhesion to the mucosae, especially the buccal mucosae, for a minimum time of 6 hours, and permitting a slow and controlled administration of melatonin exclusively via the transmucosal route.; it does not, however, permit a rapid action which is necessary in some circumstances.

Patent Application EP518468 also relates to a pharmaceutical dosage formulation affording controlled release of melatonin which is a mode of administration selected from oral, parenteral, rectal or transdermal forms.

DETAILED DESCRIPTION OF THE INVENTION

In the description which follows, the term "pharmaceutical dosage composition" or "pharmaceutical dosage formulation" will be employed without discrimination to denote any combination of constituents used for pharmacological, prophylactic or therapeutic purposes.

Melatonin undergoes a very large hepatic first-pass effect which endows it with a low or variable absolute bioavailability (measured by the ratio of the plasma melatonin concentrations and by the ratio of the areas under the respective curves). In effect, comparison of the systemic (or salivary) concentrations of melatonin after oral administration with those obtained after intravenous administration leads to a bioavailability which is highly variable from one subject to another (13).

Since the metabolites of melatonin, and especially N-acetylserotonin, 5-methoxytryptamine and 6-hydroxymelatonin which yields on conjugation 6-sulfatoxymelatonin and 6-glucuronomelatonin (14), are inactive, the outcome is a large variability in plasma melatonin concentrations and a bioavailability which is incomplete and/or variable between individuals.

Since, furthermore, the biological half-lives of melatonin are very short and in the region, according to the authors, of 10 minutes for the first half-life and 60 minutes for the second, this leads to a search for an administration system that avoids the hepatic first pass (15).

The system of the invention is a mucoadhesive, controlled-release pharmaceutical dosage composition or formulation which combines at least two layers, one (A) is mucoadhesive and permits a slow release of the active principle, and in particular of melatonin or one of its derivatives, both transmucosally and orally, in particular in the saliva if the pharmaceutical dosage composition is implanted in the mouth, the other (B) is not mucoadhesive and permits a rapid release of the active principle or principles in the lumen of the cavity in which the pharmaceutical dosage composition is implanted, and in particular in the mouth.

The target slow-transfer rates for the first layer (A) are from 0.02 mg/h to 1 mg/h depending on the applications; the target rapid-transfer rates for the layer (B) are from 0.2 mg/h to 10 mg/h depending on the applications.

The term "rapid" for the rapid-release layer is understood to mean an immediate flash release which may be sustained for 2 to 5 hours. This nonmucoadhesive layer hence makes it possible to release a certain amount of melatonin needed to give the clear chronobiological reference signal.

In other words, the mucoadhesive, double-layer pharmaceutical dosage composition of the invention has both the advantages of being pleasant to use and of being able to impart the clear chronobiological reference signal for the desired initiation of the action; this reference signal is given by a loading dose whose speed is sufficient to lead to high plasma melatonin concentrations, such that they are far greater than the response threshold of all of the subjects and become, as a result, naturally recognized as such; the release is taken over by the layer one of whose sides is mucoadhesive, which, for its part, imparts a controlled release via the mucosal or sublingual and buccal routes mentioned above; the system permits, in addition, an adhesion to the membrane for longer than 10 hours, and the system may be withdrawn at will at the desired final time leading to an immediate stopping of the effects of the melatonin.

The pharmaceutical dosage composition of the invention is especially advantageous when it is placed in the buccal cavity, but it is self-evident that it can be adaptable to any cavity covered with mucosa, such as the anal or vaginal cavities.

It is clearly apparent that this double-layer system is especially advantageous for all active compounds necessitating a flashwise rapid transmission into the circulatory system followed by a slow and controlled administration for several hours.

The double layer is one of the examples of a heterofunctional pharmaceutical dosage formulation. Other types of heterofunctional pharmaceutical dosage formulations may be employed, whose functions of rapid, semi-rapid, slow or very slow release may be combined in the same formulation: as an example, formulations such as are described in (16), in which fluidized microgranules of different formulations could be mixed and compressed with CARBOPOL® or equivalent product; the outcome of this would also be a heterofunctional mucoadhesive pharmaceutical dosage formulation combining a rapid release and a slow release of the same active principle.

A feature of the pharmaceutical dosage composition according to the invention is, more especially, that the first, mucoadhesive layer (A) contains at least:

a biocompatible polymeric resin, in particular of CARBOPOL 934P® (synthetic high molecular weight polymer or copolymer of acrylic acid) and/or polyvinylpyrrolidone (povidone) or any other biocompatible adhesive polymer, these two resins acting as adhesion agents and participating in this layer in the proportion of 35 to 80% by weight of said layer, and preferably 50 to 75% by weight, a binding or diluent agent in the proportion of 5 to 40% by weight of the mucoadhesive double layer, and preferably 10 to 30%; such an example of a binding agent is dicalcium phosphate ENCOMPRESS (dicalcium phosphate) or other binding agents of the hydroxypropylcellulose or hydroxypropylmethylcellulose type or any other type of ingredient described in the US Pharmacopeia XXII or USP XXII, pp. 1857–1859, BASF METHOCEL (hydroxypropyl cellulose and hydroxypropylmethyl cellulose) or any other retard agent of the hydroxypropylmethylcellulose type or equivalent, not necessitating the addition of water, at a weight concentration of 3 to 20%, and preferably 5 to 15%, magnesium stearate as lubricant at a maximum concentration of 1%, any type of lubricant as mentioned in the US Pharmacopeia XXII, p. 1858, which is also suitable as a component of this mucoadhesive layer, AEROSIL 200 (flow promoter of colloidal silica dioxide prepared by the vapor phase hydrolysis of a silicon compound) as flow promoter, or any equivalent such as anhydrous colloidal silica (Carboxyl, Siloid), which is added to the layer at a maximum concentration of 1%, and preferably at that of 0.2%, melatonin or one of its derivatives as are mentioned above is added at a concentration of 0.05 to 2%, and preferably 0.3 to 1.5%.

It is preferable to keep the moisture level low in the mucoadhesive layer of the pharmaceutical dosage composition of the invention.

Such a bioadhesive layer has a water content of less than 10% by weight, and preferably less than 6%, and still more preferably less than 3% of the total weight of the layer.

As will be shown in the example of implementation described later, it is hence preferable to produce the whole of this pharmaceutical dosage form in a dry atmosphere or at a relative humidity below 30%.

The rapid-release layer (B) contains at least:

a polymeric resin of the CARBOPOL® type as described above as binding agent, or any other agent providing for the same function, at a weight concentration of 2 to 15%, and preferably 8 to 12%;

a diluent of the lactose Fast Flow grade type, or any type of diluent as described in the reference table;

a disintegrating agent of the ACDISOL type (disintegrating agent consisting in cross-linked carboxymethyl cellulose), which is a crosslinked carboxymethylcellulose, at a concentration of 1 to 30%, and preferably 3 to 15%; it should be noted that, for this product, the higher the percentage, the faster the release; a percentage of 30% confers a very rapid release of the active principle, whereas a percentage of 1% gives a very slow release, of the order of 5 hours, of the active principle;

melatonin is also added to this rapid-release layer at a concentration of 0.2 to 10%, and preferably 1 to 6%.

As an option, it is possible to add a colorant in order to distinguish this layer from the other one, which colorant should be added at a maximum weight/weight proportion of 1% of the compounds of this layer.

Tables 1 and 2 below show a typical composition of each of the layers (A) and (B) of the invention containing melatonin as active principle.

TABLE 1

SUSTAINED-RELEASE MUCOADHESIVE LAYER

|  | Percentage | Unit formula | Role of the constituents | Percentage limits |
|---|---|---|---|---|
| Methocel | 10% | 15 mg | retard agent | 3–20 |
| Melatonin | 1% | 1.5 mg | active principle | variable |
| Emcompress | 22.5% | 33.7 mg | binding agent - diluent | 5–40 |

TABLE 1-continued

SUSTAINED-RELEASE MUCOADHESIVE LAYER

|  | Percentage | Unit formula | Role of the constituents | Percentage limits |
|---|---|---|---|---|
| Carbopol. 934 P ® | 65.3% | 98 mg | adhesion agent | 35–80 |
| Mg stearate | 1% | 1.5 mg | lubricant | max 1% |
| Aerosil 200 | 0.2% | 0.3 mg | flow promoter | max 1% |
|  | 100% | 150 mg |  |  |

TABLE 2

RAPID-RELEASE LAYER

|  | Percentage | Unit formula | Role of the constituents | Percentage limits |
|---|---|---|---|---|
| Ac Di Sol | 11% | 5.5 mg | disintegrating agent | 1–30 |
| Lactose Fast Flow | 74% | 37 mg | diluent | variable |
| Carbopol 934P ® | 11% | 5.5 mg | binding agent | 2–15 |
| Melatonin | 3% | 1.5 mg | active principle | variable |
| Colorant | 1% | 0.5 mg |  | max 1% |
|  | 100% | 50 mg |  |  |

Lastly, the invention relates to the use of such a pharmaceutical dosage composition as medicinal product for the treatment of sleep disturbances, for the treatment of anxiety, and in particular of seasonal anxiety, for the treatment of cancer and for counteracting aging.

The examples below, without being limiting in character, will show the great value of this type of double-layer mucoadhesive composition containing melatonin for a rapid and lasting reestablishment of the melatonin level in the plasma. This example quite obviously imposes no limitation on the use of melatonin, or on the particular composition of the double-layer composition used.

BRIEF DESCRIPTION OF THE DRAWING

In example I.

Figure 1:
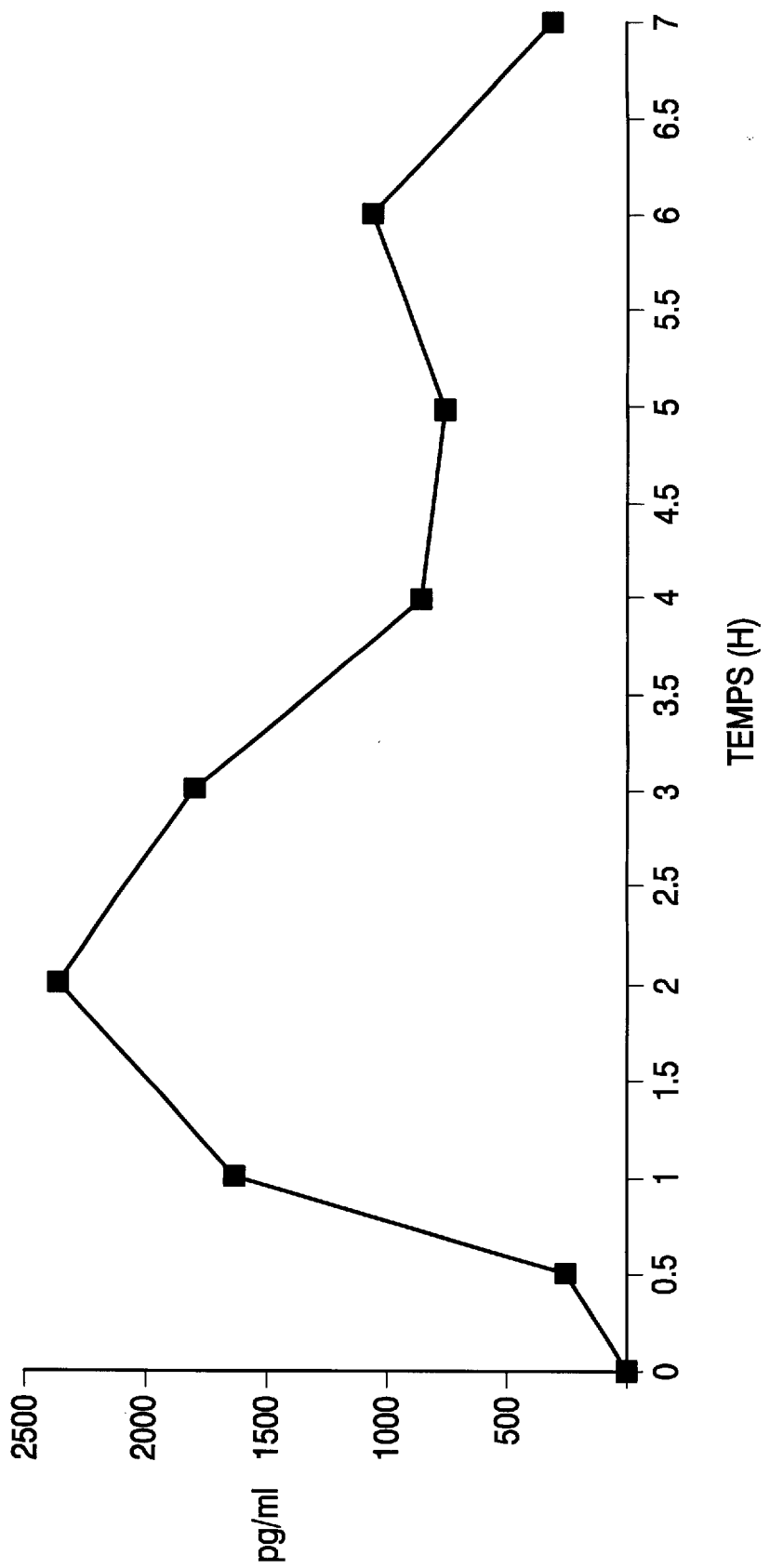
FIG. 1 shows the plasma assay on three subjects who affixed the double-layer composition inside the buccal cavity, on the inside of the lower lip, at time 0 and removed it at time 7 hours. The abscissae represent time, and the ordinates the melatonin concentration in pg/ml (picograms per milliliter).

EXAMPLE I manufacture of the double-layer mucoadhesive composition:

The process of manufacture of the double-layer mucoadhesive composition is accomplished, in a first stage, by the manufacture of the nonmucoadhesive immediate- or semi-slow-release layer, and then of the mucoadhesive layer, lastly followed by a final tableting of the two layers. It is self-evident that the variant in which the mucoadhesive layer is manufactured first, and then the immediate-release layer, followed by the final tableting of the two layers, is equivalent.

The composition produced in the example which follows is that shown in Tables 1 and 2 as regards the percentages of each of the constituents.

Manufacture of the rapid- or semi-slow-release layer:

Lactose Fast Flow, Carbopol® (sieved beforehand), melatonin and the colorant are introduced into a Turbula or equivalent mixer; the constituents are mixed for 10 minutes.

Ac Di Sol or any other equivalent disintegrating agent is then added and the constituents are mixed for 10 minutes.

The mixture is then stored in a suitable contained and weighed.

Manufacture of the mucoadhesive layer:

This layer is made by granulation by the dry method, and comprises the following steps:

1. Carbopol 934P® is introduced into a Turbula mixer with the flow promoter (Aerosil), the constituents being mixed for 5 minutes.

2. The mixture is then sieved through a screen of diameter 500 µm.

3. The mixture thus sieved is introduced into a Turbula type mixer and mixed for 3 minutes.

4. Melatonin is then added to the above mixture, as well as Methocel, and stirred for 10 minutes.

5. Half of the magnesium stearate or other equivalent lubricant, sieved beforehand, is then added, and the constituents are mixed for 3 minutes.

6. The mixture is then recovered, weighed and stored in a suitable container.

Compaction or first tableting:

7. The mixture of step 6 is introduced into the feed hopper of a compacter.

8. The "pebbles" of step 7 are granulated on an Erweka or equivalent type granulator equipped with a screen of diameter 1 mm.

9. The granule of step 8 is introduced into a Turbula type mixer; Emcompress is added and the constituents are mixed for 10 minutes.

10. The second half of the lubricant, for example magnesium stearate, sieved beforehand, is added to the mixture of step 9, and the constituents are mixed for 3 minutes.

11. This mixture 10 is stored in a suitable container and weighed.

Production of the mucoadhesive layer: second tableting:

12. The granule of step 11 is reworked and introduced into the feed hopper of the compacting machine, and tableting is thus initiated. For this step, the tablets should have sufficient hardness to have a friability of less than 1%, but a capacity for tableting must exist in order to enable the final tablet to be produced.

Final tableting:

1. The mucoadhesive tablets are introduced into the first feed hopper, and the immediate-release type mixture is introduced into the second hopper.

2. The amount of powder needed to feed the tableting chamber is adjusted.

3. Final tableting is carried out with monitoring of the hardness and weight of the final composition.

The whole of this manufacture should be carried out in a dry unit, that is to say at an RH below 30%.

EXAMPLE II effect of the administration of the pharmaceutical dosage composition of the invention on the plasma melatonin level of normal subjects:

Plasma melatonin concentrations were studied in 3 individuals treated with the tablet presented in Example I.

Three subjects, namely 2 men and one woman 31, 50 and 50 years of age, respectively, had melatonin concentrations on day D-1 at T0 (9.30 a.m.), T0+1 h (10.30 a.m.) and T0 +4 h (1.30 p.m.) below the limit of quantification of the RIA method described below. Next day, on D0, they applied at T0 (9.30 a.m.) the mucoadhesive tablet inside the lower lip at the height of the incisor, and kept it until time T0+7 h (4.30 p.m.).

The tablet contained a 1.5 mg dose of melatonin in the programmed-release mucoadhesive layer and a 1.5 mg dose of melatonin in the outer or loading dose layer.

Blood samples were drawn into heparinized tubes at times T0 (before installation of the tablet) and T0 +0.5 h, T0+1 h, T0+2 h, T0 +3 h, T0 +4 h, T0+5 h, T0+6 h and T0 +7 h. After centrifugation and collection of the plasma, a melatonin assay was carried out by an RIA method (17, 18), in which the antibodies are obtained from Stock Grand (UK) with tritiated tracer (Amersham). This method permits a determination of concentrations between 10 pg/ml and 200 pg/ml. The limit of quantification was 10 pg/ml. Appropriate dilutions were prepared for assaying the plasma melatonin concentrations on the three profiles.

The measured concentrations were as follows (see table below), and the curve in FIG. 1 shows the subjects' mean concentration.

| Time (h) | Mean concentration (pg/ml) |
| --- | --- |
| 0 | 0 |
| 0.5 | 254 |
| 1 | 1632 |
| 2 | 2375 |
| 3 | 1790 |
| 4 | 850 |
| 5 | 750 |
| 6 | 1050 |
| 7 | 283 |

It was demonstrated that the diurnal melatonin concentrations are low, which was verified on the 3 subjects for which the concentrations were below the limit of quantification (<10 pg/ml) on D-1. Since the administration was carried out on D0 from 9.30 a.m. to 4.30 p.m., the plasma concentrations encountered in these 3 subjects are a reflection of the exogenous melatonin administered by the mucoadhesive tablet.

The tablet was fully tolerated, no discomfort being experienced a quarter of an hour after it was installed and up to the time of its removal. The subjects felt sleepy 2 h after installation of the tablet, characterized in the 3 subjects by the desire to take a nap in one case, unaccustomed yawning in another and the sensation of having slept for 3 hours the previous night (in spite of a good night's sleep) in the last. No discomfort was experienced in eating a meal from 1 p.m. to 1.30 p.m. (drink and food). The tablet was removed by mechanical action of the finger. This administration resulted in no general or local side-effect, showing an excellent clinical tolerability of the tablet.

CONCLUSION

Such pharmaceutical dosage compositions as described above in the invention are especially advantageous on several grounds.

The first is the convenience of use, since compounds which adhere to the inside of the mouth on the mucosa are relatively stable, permit normal eating and are not uncomfortable for the subjects.

Another advantage is that, immediately the tablet is removed, the plasma melatonin concentrations decrease and fall below the limit of quantification.

The essential advantage is clearly apparent from inspection of FIG. 1, which shows unmistakably the immediate flash effect conferred as a result of the nonmucoadhesive layer (B), followed by a controlled and continuous release as a result of the second, mucoadhesive layer. By way of comparison, this curve may be compared with the curves given, for example, in Patent EP 518468, in which the appearance of melatonin in the plasma is relatively slow, mimicking the normal cycle of appearance and disappearance during the night.

The plasma kinetics of melatonin given in FIGS. 5 and 6 of Patent Application WO93/07870 reveal a slow increase in the melatonin concentration in the plasma (see, in particular, FIG. 6 and FIG. 8 of said patent).

The same observation may be made regarding the plasma kinetics of melatonin obtained from the bioadhesive composition described in Patent Application WO91/06290, which show a slow and continuous increase in melatonin in the plasma as a result of the sustained release of the active principle.

No system has shown the twofold advantage of immediate transfer followed by a semi-slow and controlled release throughout the period of maintenance of the pharmaceutical dosage composition of the invention on the mucosa.

BIBLIOGRAPHY

1. Lewy A. J., Wehr T. A., Goodwin F. K., Newsome D. A., Markey S. P., 1980. Light suppresses melatonin secretion in humans. Science 210:1267.

2. Arendt J., Broadway J., 1987. Light and melatonin as zeithcibers in man.

3. Arendt J., Aldhous M., English J., Marks V., Arendt K. H., Marks M; and Folkard S., 1987. Some effects of jet lag and their alleviation by melatonin. Ergonomics, 30:1379.

4. Samel A., Maas H., Vejroda M., Wegman H. M., 1989. Influence of melatonin treatment on human circadian rythmicity. in "Aviation, Space and Environmental Medicine" Abst 485, p. 52.

5. Nickelsen T., Land A., Bergau L., 1991. The effect of 6-, 9- and 11-hour time shifts on circadian rhythms: adaptation of sleep parameters and hormonal patterns following the intake of melatonin or placebo. In "Advances in Pineal Research: 5", Arendt J., Pévert P. (Eds), John Libbey & Co Ltd., p. 306.

6. Folkard S., Arendt J., Clark M., 1990. Can melatonin improve shift workers' tolerance of the night shift? Some preliminary findings. Interdisciplinary Cycle Research, Proceeding of the European Society for Chronobiology.

7. Aldhous M., Arendt J., 1991. Assessment of melatonin rhythms and the sleep-wake cycle in blind subjects. in "Advances in Pineal Research:5", Arendt J., Pévet P. (Eds), John Libbey & Co Ltd., p. 307.

8. Tzischinsky O., Dagan Y., Lavie P., 1993. The effects of melatonin on the timing of sleep in patients with delayed sleep phase syndrome. in "Melatonin and the pineal gland"—from Basic Science Publishers P.V., p. 351.

9. Touitou Y. et al., 1981. "Age- and Mental Health-Related Circadian Rhythms of Plasma Levels of Melatonin, Prolactin, Luteinizing Hormone and Follicle-Stimulating Hormone in Man", J. Endocr. 91:467–475.

10. Tamarkin L., Almeida O. F. X., Danforth D. N., 1985. Melatonin and malignant disease.

11. Blask D. E., 1993. Melatonin in oncology. In "Melatonin: biosynthesis, physiological effects, and clinical applications", Yu H. S., Reiter R. J. (Eds), CRC Press, Boca Raton, Fla., p. 447.

12. Wirz. Justice et al. (1990). J. Psychiat. Res. 24(2):129–137.

13. Waldhauser F., Waldhauser M., Lieberman R. et al., 1984. "Bioavailability of Oral Melatonin in Human". Neuroendocrinology 39:307,313.

14. Hing Sing Yu 1993.

15. Mallo C., Zaïdan R., Galyg et al. 1990. "Pharmacokinetics of Melatonin in Man after Intravenous Infusion and Bolus Injection". Eur. J. Clin. Pharmacol. 38:297–301.

16. RITSCHEL W. A. et al. Peroral solid dosage forms with prolonged action in DRUG DESIGN, vol. 4 (E. J. ARIEN Ed.), Academic New York, 1973, chap. 2, p. 37.

17. Arendt J., Sizonenko P. C., Pauniner L. "Melatonin Radioimmunoassay". 1975. J. Clin. Endocrinol. Metab. 40:347–350.

18. Howanitz P. J., Howanitz J. H. 1983. "Direct Radioimmunoassay for Melatonin in Plasma". Clin. Chem. No. 2, 29:396–397.

I claim:

1. A mucoadhesive controlled-release dosage pharmaceutical formulation comprising at least one active principle selected from the group consisting of melatonin and melatonin derivatives; and composed of a a first layer and a second layer, said first layer being mucoadhesive and permitting a sustained release of the active principle at a rate of 0.02 mg/h to 1 mg/hr both transmucosally and orally, and said second layer being nonmucoadhesive, permitting a release of the active principle at a rate of 0.2 mg/h to 10 mg/h, wherein said first layer comprises at least:

a biocompatible acrylic acid polymeric resin adhesion agent in a concentration of 35 to 80 weight %, a hydroxymethylcellulose or hydropropylcellulose diluent binding agent in a concentration of 5 to 40 weight %, a hydropropylmethylcellulose retard agent in a concentration of 3 to 20 weight %, a magnesium stearate lubricant in a maximum of 1% by weight, a flow promoter at maximum concentration of 1 weight %, and said at least one active principle;

said second layer comprises at least:

an acrylic acid or polyvinyl pyrrolidone polymer at a concentration of 2 to 15 weight %, a disintegrating agent at a concentration of 1 to 30 weight %, said at least one active principle;

a lactose diluent in a concentration of from 60 to 80 weight %, and optionally, a colorant at a maximum concentration of 1 weight %.

2. The formulation according to claim 1, wherein said melatonin, or derivative thereof, is in an amount of 0.05 to 2 weight %.

3. The formulation according to claim 1, wherein said melatonin, or derivative thereof, is in an amount of 0.3 to 1.5 weight %.

4. The formulation according to claim 1 wherein the retard agent is present at a concentration of 8 to 12 weight %.

5. The formulation according to claim 1 wherein the diluent binding agent is present at a concentration of 15 to 30 weight %.

6. The formulation according to claim 1, wherein the adhesion agent is a synthetic high molecular weight polymer or copolymer of acrylic acid at a concentration of 45 to 75 weight % in said first layer and 8 to 12 % in said second layer.

7. A method of rapid and sustained restoration of an active principle selected from the group consisting of melatonin and melatonin derivatives, in a mammal comprising administering the formulation of claim 1 to said mammal.

8. A method of rapid and sustained restoration of an active principle selected from the group consisting of melatonin and melatonin derivatives, in a mammal comprising administering the formulation of claim 2 to said mammal.

9. A method of rapid and sustained restoration of an active principle selected from the group consisting of melatonin and melatonin derivatives, in a mammal comprising administering the formulation of claim 3 to said mammal.

10. The method according to claim 7 wherein said mammal is a human in need of treatment for sleep disturbances.

11. The method of claim 7 wherein said mammal is a human in need of treatment of anxiety.

12. The method of claim 11 wherein said anxiety is seasonal anxiety.

13. The method of claim 7 wherein said mammal is a human.

14. The formulation according to claim 11 wherein said active principle is melatonin.

* * * * *